United States Patent [19]

Manser

[11] Patent Number: 4,483,978
[45] Date of Patent: Nov. 20, 1984

[54] ENERGETIC COPOLYMERS AND METHOD OF MAKING SAME

[75] Inventor: Gerald E. Manser, Cupertino, Calif.

[73] Assignee: S R I International, Menlo Park, Calif.

[21] Appl. No.: 379,354

[22] Filed: May 18, 1982

Related U.S. Application Data

[63] Continuation-in-part of Ser. No. 262,935, May 12, 1981, Pat. No. 4,393,199.

[51] Int. Cl.$^3$ .............................................. C08G 65/22
[52] U.S. Cl. ..................................... 528/408; 149/88; 260/349; 528/417
[58] Field of Search .................. 528/408, 417; 260/349

[56] References Cited

U.S. PATENT DOCUMENTS

| | | | |
|---|---|---|---|
| 3,112,280 | 11/1963 | Farthing | 528/408 |
| 3,347,801 | 10/1967 | Stogryn | 528/417 |
| 3,557,181 | 1/1971 | Lakritz et al. | 528/408 |
| 3,645,917 | 2/1972 | Vandenberg | 528/417 |
| 4,250,294 | 2/1981 | Hagel et al. | 528/417 |
| 4,268,450 | 5/1981 | Frankel et al. | 528/417 |
| 4,405,762 | 9/1983 | Earl et al. | 528/408 |

FOREIGN PATENT DOCUMENTS 758450 10/1956 United Kingdom ............... 528/408

*Primary Examiner*—Wilbert J. Briggs, Sr.
*Attorney, Agent, or Firm*—Edward B. Gregg; Urban H. Faubion

[57] ABSTRACT

Energetic copolymers having repeating mer units derived from different monomers, one or both of which have pendant energetic groups such as azido, nitro or nitrato groups. Copolymers have improved formulating characteristics compared to homopolymers of the energetic monomers; e.g., they are less crystalline or less viscous. Preferably the monomers are cyclic oxides having three to six atoms in the ring. The energetic monomers are preferably azido, nitro or nitrato derivatives of oxetane or THF. Copolymerization is preferably carried out by cationic polymerization using an adduct of the preinitiator precursor (e.g., 1,4-butane diol) and a catalyst suitable for cationic polymerization (e.g., boron trifluoride etherate) which is employed in stoichiometric proportion to the monomers and a low molecular weight, low polydispersity copolymer results. Certain novel monomers also are provided.

10 Claims, 3 Drawing Figures

ENERGETIC COPOLYMERS AND METHOD OF MAKING SAME

DESCRIPTION

This work was done during the course of Office of Naval Research Contract No. N-00014/79/C/0525.

This application is a continuation-in-part of my copending application Ser. No. 262,935 entitled "Cationic Polymerization" filed May 12, 1981, now U.S. Pat. No. 4,393,199.

FIELD OF THE INVENTION

This invention relates to energetic copolymers containing repeating mer units derived from cyclic oxides at least some of which have energetic substituents. Such polymers have military and civilian uses as explosives, as propellants and as gasifiers.

DESCRIPTION OF THE PRIOR ART

Representative of energetic homo polymers are polymers of bis-(azidomethyl) oxetane which has the formula

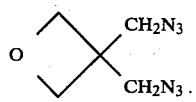  1

When this monomer is homopolymerized it results in a polymer as follows:

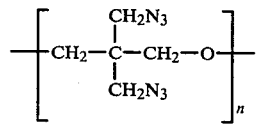  2

Other energetic substituents include nitro groups ($-NO_2$) and nitrato groups ($-O-NO_2$).

Preparation of the monomer 1 and of the homopolymer 2 are described in Carpenter, U.S. Pat. No. 3,138,609. The controlled polymerization of this monomer to produce low molecular weight polymers of low polydispersity is described in my copending application Ser. No. 262,935 filed May 12, 1981, entitled "Cationic Polymerization." Control of molecular weight and achievement of low polydispersity are effected by use of an adduct of a catalyst and an alcohol.

The polymer 2 is energetic by reason of the azido groups which decompose at elevated temperatures to produce nitrogen. Such decomposition commences at about 180° C. The maximum exotherm occurs at about 250° C. This and other polymers with pendant azido groups decompose without combustion at atmospheric pressure. At a sufficiently high pressure the decomposition is accompanied by combustion. Similarly polymers with pendant nitro and nitrato groups undergo decomposition.

Such polymers are useful as energetic binders for rocket propellants. They may, for example, be copolymerized with a trifunctional substance such as trimethylolethane and tolylene diisocyanate to produce a binder for a rocket propellant such as a mixture of aluminum powder and HMX. An advantage of such a binder is that the pendant energetic groups contribute energy.

However, polymers such as 2 above are crystalline, or if not crystalline they are very viscous at normal formulating and working temperatures, e.g., room temperature or somewhat higher.

SUMMARY OF THE INVENTION

It is an object of the present invention to provide energetic polymers similar to 2 which are sufficiently fluid at acceptably low temperatures to be formulated and fabricated.

The above and other objects are attained in accordance with the present invention by copolymerizing an energetic cyclic oxide monomer such as 1 above with a different cyclic oxide monomer.

The azido monomer (Monomer I) which is to be polymerized may be represented by the formula

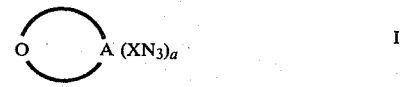  I wherein A represents an alkylene group containing two to five carbon atoms, X represents a valence bond (where the azido group $N_3$ is attached directly to a ring carbon atom) or a short chain alkylene group such as $>CH_2$, $-CH_2CH_2-$, etc. and the subscript a is a small integer, usually one or two. Monomer I is capable of homopolymerization to provide a polymer such as 2. It will be understood that nitro or nitrato groups may replace the azido groups. Hereinafter where azido groups are mentioned it will be understood that other energetic groups, exemplified by nitro and nitrato, may be used.

In accordance with the present invention Monomer I is copolymerized with a cyclic oxide (Monomer II) which may be represented by the formula

  II wherein B is an alkylene group (which may be variously substituted) containing two to five carbon atoms. The requirements of Monomer II are that it undergo copolymerization with Monomer I and that it differ from Monomer I sufficiently that there results a copolymer

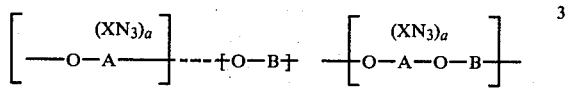  3 which has insufficient stereo regularity to form a crystalline product (or such that the tendency to form crystals is greatly diminished). As a result an energetic copolymer is produced which can be readily formulated and fabricated. Monomer I may be such that its homopolymer is not crystalline but has an unacceptably high viscosity at normal formulation and fabrication temperatures, e.g., room temperature or somewhat higher. In such a case copolymerization with Monomer II will result in a copolymer having a lower viscosity. This is so even where each monomer homopolymerizes to produce a crystalline or very viscous polymer.

DETAILED DESCRIPTION OF THE INVENTION

The mer unit (1)

Figure 1:
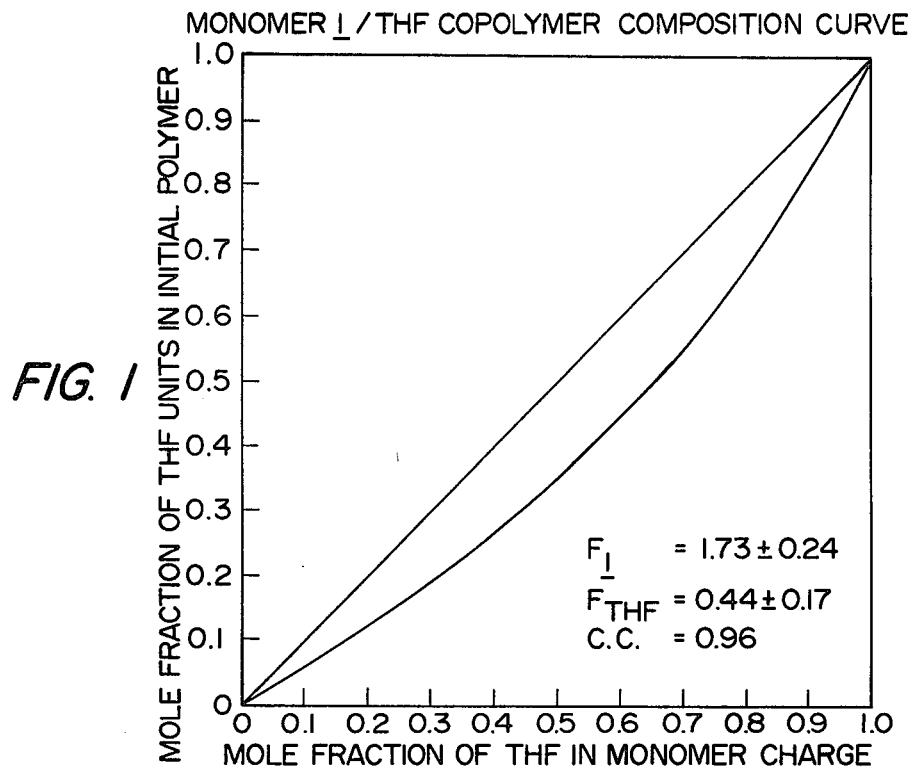

$$-O-A-$$
$$(XN_3)_a$$

and the mer unit (2) —O—B— may be present in widely varying molecular proportions, for example, 10 percent or less of (1) and 90 percent or more of (2) to 90 percent or more of (1) and 10 percent or less of (2).

The distribution (whether random or otherwise) of the mer units (1) and (2) in the polymer molecule will depend upon a number of factors such as the molar proportions of the monomers and the reactivities of the monomer. Polymerization may be carried out in accordance with methods in the prior art resulting in a polymeric product having a wide distribution of molecular weights (i.e., a product of high polydispersity). Preferably, however, controlled polymerization by the method of cationic polymerization described in my copending patent application is employed. Such technique results in a polymeric product of low polydispersity and it employs an adduct of a substance such as a diol (e.g., 1,4-butane diol, BDO) and a catalyst for cationic polymerization (e.g., $BF_3$ etherate). This adduct forms with the monomer (in this instance Monomer I or Monomer II or a mixture of the two) an initiating species which undergoes chain extension until n mols of monomer have been incorporated in the molecule, n being the ratio of mols of monomer to adduct. Usually n is a relatively small number, such as 10 or 20, and the product is an oligomer of low polydispersity, e.g., 1.1 to 1.2.

Such controlled cationic polymerization is preferred for several reasons. One reason is that it greatly diminishes unwanted products such as cyclic oligomers. Also it produces polymers having a functionality of two capable of chain extending with, for example trimethylol ethane and a diisocyanate.

Also, if block polymers, e.g.

or

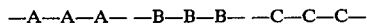

are desired (A, B and C representing mer units from different monomers) it is possible to prepare them by the method of application Ser. No. 262,935.

The preferred Monomer I contains three to four carbon atoms in the cyclic oxide ring. That is, it is a derivative of oxetane or of tetrahydrofuran (THF). Likewise the preferred Monomer II contains three to four carbon atoms in the oxide ring and is therefore oxetane or THF or a derivative of oxetane or THF.

Monomer I is an energetic monomer and imparts energetic characteristics to the polymer. It will be understood that "energetic" refers to the energy released by decomposition of the azido group. That is to say, apart from heat of combustion an energetic monomer and an energetic polymer have a positive heat of decomposition. If Monomer II is itself an energetic monomer it will, of course, contribute to the energetic quality of the polymer but if it is not an energetic monomer, for example, if it is oxetane or THF, it will not make such a contribution and will diminish the energetic property of the polymer.

A symmetrical Monomer I such as

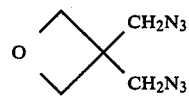

1

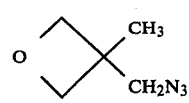

4

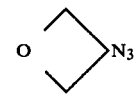

5 will homopolymerize to a polymer having stereo regularity such as

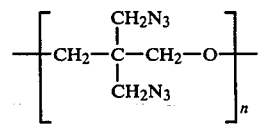

6

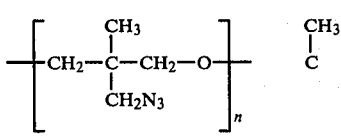

7

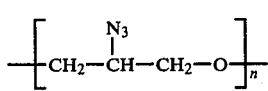

8

The insertion by copolymerization of a different mer unit will break up the stereo regularity and will eliminate or diminish the crystalline character of the polymer. This occurs even where both monomers give rise to crystalline or semi-crystalline polymers. A case in point is the copolymer of 1 and THF. Both monomer 1 and THF homopolymerize to a crystalline polymer but their copolymers are not crystalline or are much less so.

The same result may be achieved by appropriate selection of an asymmetric Monomer I without the use of a separate Monomer II. Representative of such asymmetric monomers are the following

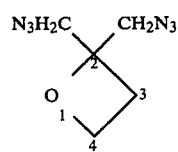

9

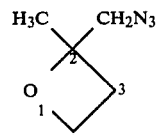

10

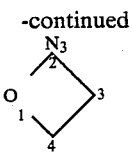

Upon polymerization the ring may be broken between the one and two positions or between the one and four positions leading to the production, from a single monomer of two different monomeric species which will then copolymerize to provide a polymer having the desired lack of, or a low degree of crystallinity. In the instances given above, the resulting polymers will have structures exemplified by the polymer of monomer 9:

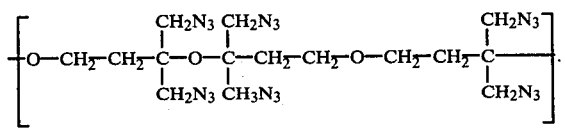

SPECIFIC EXAMPLES

The following specific examples will serve further to illustrate the practice and advantages of the invention.

EXAMPLE 1

Materials

Burdick and Jackson UV grade THF was dried by storing over 4A molecular sieve. Commercial grade boron trifluoride etherate was freshly distilled prior to use. 1,4-butanediol was distilled from calcium hydride and stored over 4A molecular sieve.

3,3-Bis(azidomethyl)oxetane (1) was prepared by heating a solution of one mole 3,3-bis(chloromethyl)oxetane and two moles sodium azide in dimethylformamide at 80° C. for 18 hours. After cooling, the precipitated sodium chloride was removed by filtration and the filtrate vacuum distilled to give 130 g (80% yield) of 1, bp 78° C./0.2 Torr. Caution: Allowing the hot pot residue to contact air may result in a violent detonation. Purification of 1 by column chromatography (methylene chloride, basic alumina) is the method of choice. The preparation of this monomer is also described in Carpenter U.S. Pat. No. 3,138,609.

It is important that dry materials and dry conditions of reaction prevail. The other monomer was THF.

Polymerization Procedure

The copolymerizations were run in a jacketed 100-ml glass resin flask equipped with a mechanical stirrer. In each case 0.25 moles of monomer mixture, 0.025 moles $BF_3$ etherate, and 0.0125 mole butanediol were used. (The term "mole" refers to gram mole.) The THF, butanediol, and $BF_3$ etherate were combined and stirred for 30 minutes. (THF does not undergo appreciable polymerization by itself under these conditions.) The mixture was then cooled to $-5°$ C. and the monomer 1 was added. After stirring for 48 hours, the reaction was quenched with saturated aqueous sodium chloride. The crude polymer was separated, dissolved in a minimum volume of methylene chloride and reprecipitated by addition to a tenfold volume of methanol. The reprecipitated polymer was isolated by decanting the methanol and drying in vacuo.

Molecular Weight Determination

Number average and weight average molecular weights of polymer were determined using a Waters gelpermeation chromatograph equipped with four microstyragel columns (100Å, 500Å, $10^3$521, $10^4$Å), a differential refractive index detector, and a Data Module 730. The columns were calibrated with polypropylene glycol standards of molecular weight 800, 1200, 2000, and 4000.

Measurements of Reactivity Ratios

The reactivity ratios of THF and monomer 1 were determined by the Kelen-Tudos method. The disappearance of monomer was monitored by gas chromatography, using a glass column packed with 10% OV-101 on Chrom Q. Samples were periodically removed from the reaction mixture and quenched by dissolution in wet methylene chloride. At the end of the reaction the copolymer was isolated and purified as described above and characterized by its NMR spectrum and elemental analysis. The Kelen-Tudos method is described in J. Macromol. Science-Chem, A9(1), pp. 1–27 (1975); J. Polymer Sci., 13, 2277–2289 (1975), and J. Polymer Sci., 15, 3057–3074 (1977).

The properties of the polymers obtained from these copolymerizations are shown in Table 1.

TABLE 1

| POLYMER PROPERTIES OF POLYMER 2 | | | | | |
|---|---|---|---|---|---|
| Mole Fraction of Monomer Charge | | | | | Molecular |
| Monomer 1 | THF | MP °C. | Density g/cc | Functionality —OH/molecule | Weight $M_w$ |
| 0.00 | 0 | 78 | 1.30 | 1.9 | 6500 |
| 0.75 | 0.25 | 50 | 1.24 | 2.0 | 6900 |
| 0.60 | 0.40 | 25 | 1.27 | 2.0 | 6200 |
| 0.50 | 0.50 | <0 | 1.18 | 2.0 | 7300 |

These products were obtained in high yield and were low molecular weight oligomers of low polydispersity. The 50/50 mole % copolymer is a mobile oil at ambient temperature, and its viscosity is relatively low compared to polymers of higher monomer 1 content. The 50/50 copolymer had the best overall physical properties for a binder application.

A gumstock was prepared from the 50/50 copolymer by mixing with trimethylolethane to achieve the required crosslink density of 10% and then condensed with one equivalent of tolylene diisocyanate. The sample was cured for 24 hours at 65° C.

The room temperature stress/strain curve of the 50/50 copolymer gumstock obtained at a strain rate of 0.02 in/min, gave an engineering stress at break of $7.93 \times 10^6$ dyne/cm² (115 psi). Elongations of up to 425% were observed. Equilibrium swelling measurements in THF gave an average molecular weight between crosslinks of about 89,000. Dynamic tensile moduli measurements at 110 Hz indicated that the $T_g$ of the gumstock was $-56°$ C. Differential scanning calorimetry (20° C./min) showed only a single exotherm that began at 210° C. and reached a maximum at 254° C.

EXAMPLE 2

In this example the quantities were increased. One gram mol of monomer 1 and one gram mol of THF were employed. It was found that stirring became easier with the larger batch size. Viscosity was more troublesome on the smaller scale of Example 1. Polymerization temperature was considered the most important parameter for high monomer conversion. It is known that the conversion of THF to polymer is 89% at 0° C., 72% at 30° C. at 0% at the ceiling temperature of 85° C. The polymerization temperature employed was at −5° C. Four methods of polymer preparation were employed.

(a) In the first method the preinitiator was prepared by reaction of BDO with $BF_3 \cdot Et_2O$ in THF. This formed a preinitiator as described in my copending application Ser. No. 262,935. Monomer 1 was then added to the THF solution over a 15-minute period. A rapid uptake of monomer 1 and THF was observed over the first hour at which point the rate of THF uptake decreased. After 5 hours 75% monomer 1 and 55% THF had been converted. After 20 hours monomer 1 had reached a steady state of 98% conversion whereas THF reached a steady state of 85% after 38 hours. Based on the amount of monomers remaining, the final polymer composition was calculated to be 56% monomer 1/44% THF.

Due to the difference in reactivity of THF and monomer 1 one could expect that the head of the polymer chain would be rich in monomer 1 and the tail rich in THF. However, during the middle 60% of the polymerization time a 1:1 monomer uptake was observed.

(b) A second method of preparation was examined in order to achieve a more random copolymer: Monomer 1 was added dropwise to the THF preinitiator solution over the entire run of 42 hours. In this case nearly 3 hours passed before monomer 1 was in high enough concentration to take part in the polymerization, whereas 30% of the THF had polymerized. However, once monomer 1 began to polymerize the ratio of monomer uptake was 1:1. This rate of uptake continued for 23 hours at which time the THF level decreased to a point where monomer 1 homopolymerization predominated. After 45 hours, a steady state was achieved, indicating a final 87% THF and 96% monomer 1 uptake. The resultant polymer was similar to that obtained when monomer 1 and THF were added simultaneously, that is, a head rich in monomer 1 and a tail rich in THF. It should be noted that because THF was in excess during most of the run, the polymerization viscosity was relatively low until the final 2 hours when the viscosity approached that observed in the previous run.

(c) A third method, namely solution polymerization, was examined in an attempt to reduce the polymerization viscosity. It is known that oxetanes readily polymerize in solution whereas tetrahydrofuran polymerization is hindered. THF homopolymerization to 90% conversion is attained in bulk, but only a 27% conversion is achieved at room temperature in a 60% dichloromethane solution. However, the use of nitromethane is reported to effect higher conversions. Consequently a monomer 1 copolymerization was run in nitromethane. After 24 hours, analysis showed that the polymerization had achieved a steady state of 98% conversion of monomer 1 and 52% of THF.

(d) A fourth method of polymerization was examined in which all monomers and catalyst were stirred in the absence of a solvent at −5° C. for 30 minutes and then allowed to polymerize for 40 hours without further stirring. After quenching, the resulting polymer was found to be identical in all respects to those obtained previously. As this method of polymerization alleviates the problems associated with stirring increasingly viscous material it is considered the method of choice for scale-up.

EXAMPLE 3

Gumstocks were prepared from bulk-polymerized 50/50 monomer 1/THF polymers of Example 2(d). The polymer was mixed with trimethylolethane to achieve the required crosslink density and then with one equivalent of tolylene dissocyanate, which is the amount required to give an infinite network. After curing 24 hours at 65° C. the samples were subjected to various tests.

The stress/strain curve, obtained by Instron measurement, gave a value of 115 psi at 425% elongation at a crosslink density of 10%. An average of 89,000 molecular weight between crosslinks was determined by swelling experiments. A Rheovibron study showed a classical E' curve for an elastomer from −80° C. to room temperature and the E" curve showed a single deflection at −54° C. corresponding to the glass transition temperature. Differential scanning calorimetry showed a flat trace until the onset of an exotherm starting at 210° C. and maximizing at 254° C.

EXAMPLE 4

In this example two energetic monomers were copolymerized. These monomers were monomer 1 and 3-azidomethyl-3-methyl oxetane (monomer 4) which has the following structure

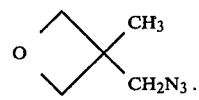

Monomer 4, which is a new compound, was prepared by different methods, as follows:

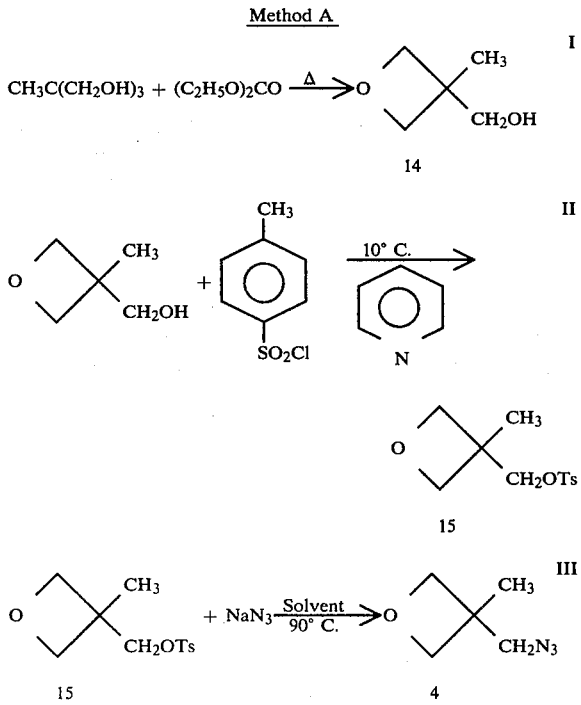

3-hydroxymethyl-3-methyl oxetane (14) is prepared in 89% yield by the method of Searles et al., JACS, 82, 2930 (1960) as shown in equation I.

The tosylate 15 is prepared in 100% yield as shown in equation II if the reaction is carried out at 10° C. or less. Ring hydrolysis occurs if the reaction is run at room temperature, thus lowering the yield.

Azidification is performed (equation III) by the act of sodium azide in a suitable solvent at 90° C. DMF, DMSO and ethylene glycol have been used as solvents, the highest yield (75%) having been obtained with DMSO.

Method B

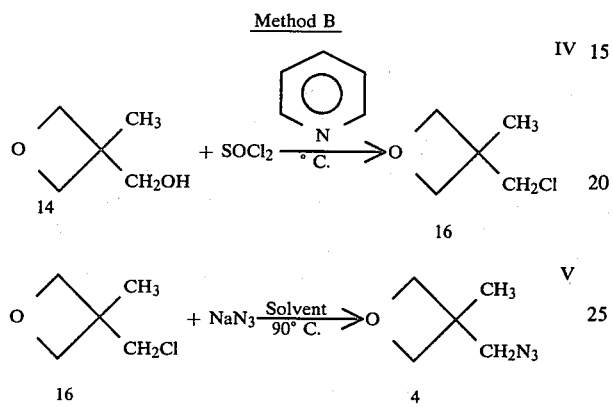

IV

V

Azidification shown in equation V proceeds in a 50% yield.

Method C

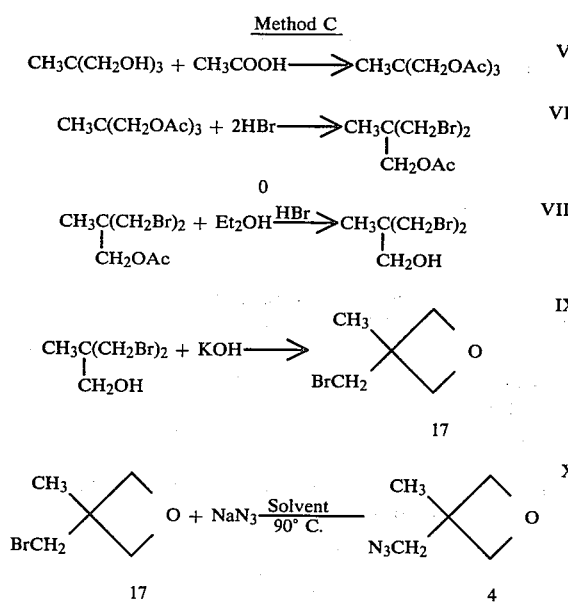

VI

VII

VIII

IX

X

Reaction scheme C is designed to prepare halo derivative of the oxetane alcohol 17 without subjecting the ring to possible hydrolysis. The oxetane is formed by ring closure (equation IX) of the dibromo alcohol with potassium hydroxide.

Figure 2:
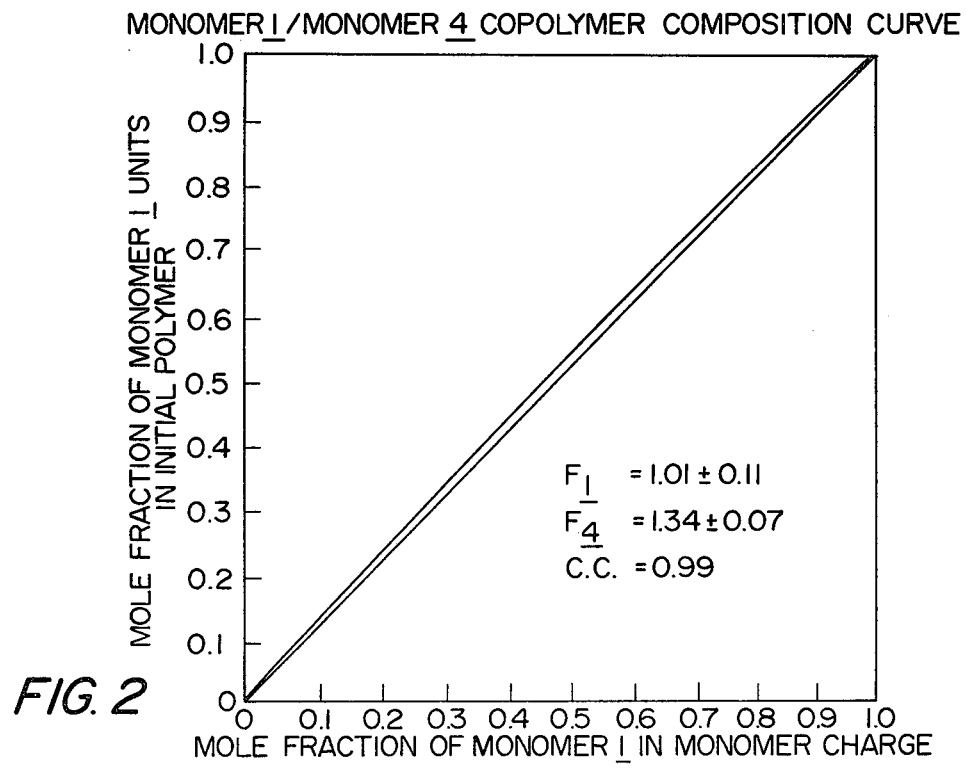

Monomer 4 was homopolymerized and it was copolymerized with monomer 1 using the procedure of copending application Ser. No. 262,935 and essentially that of Example 1 above. The homopolymer of 4 was crystalline. The copolymer of a 50/50 mol percent mixture of 1 and 4 resulted in a viscous oil which was readily pourable at 30° C. The instantaneous polymer composition curve of mixtures of 1 and 4 is shown in FIG. 2 which is discussed in Example 7 below.

EXAMPLE 5

Monomer 5 was copolymerized with monomer 1. Monomer 5 was prepared by the method described in Report No. ONR-2-3 (Interim), "Research in Energetic Compounds," sponsored by The Office of Naval Research, Contract N00014-78-C-0147, dated January, 1981, the authors being K. Baum, P. T. Berkowitz and W. A. Vinson. Copolymerization was carred out using the procedure of my copending application. The polymer resulting from a 50/50 mol percent mixture of 1 and 5 was a viscous oil readily pourable at 30° C.

EXAMPLE 6

The following novel monomers have been synthesized:

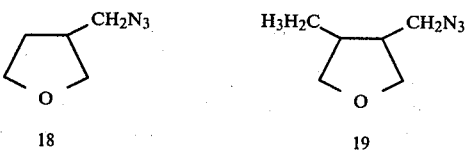

18    19 namely 3-azidomethyl THF (18) and 3,4-bis-(azidomethyl) THF (19). They were prepared as follows:

Monomer 18

Furan-3-methanol was reacted with dihydropyran to produce the tetrahydropyranyl ether. This is a conventional step carried out to protect the hydroxyl group. Other vinyl ethers may be used in place of dihydropyran. The ether was reduced by hydrogen at 1100 psi at 120° C. using a commercially available 56% nickel catalyst. The resulting product was subjected to hydrolysis in acid solution to produce the alcohol 20:

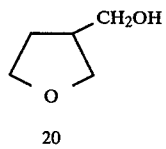

20 which is believed to be a new compound. The corresponding tosylate was prepared by treatment of 20 with tosyl chloride and the tosylate was reacted with sodium azide in DMF at 95° C. for 24 hours.

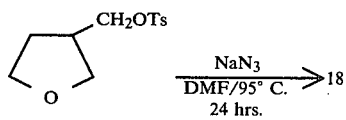

Monomer 18 was a colorless liquid which, on distillation formed a 1:1 molar complex with DMF which boils at 78° C./15 mm.

Monomer 19

Furan-3,4-dimethanol was reduced to 3,4-dimethylol THF which in turn was converted to the ditosylate 21, such steps being carried out as in U.S. Pat. No.

3,855,237. This ditosylate was treated with sodium azide in DMF at 95° C. for 24 hours.

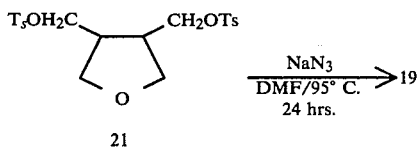

Monomer 19 was a colorless liquid boiling at 68° C./0.01 mm.

The structures 18 and 19 were confirmed by infra red, nmr and chemical analysis. They can be homopolymerized or copolymerized by conventional methods or, preferably, by the method of U.S. patent application Ser. No 262,935. Copolymerization can be with THF or any other species of Monomer II. Also, monomers 18 and 19 can be copolymerized with one another.

EXAMPLE 7

Figure 3:
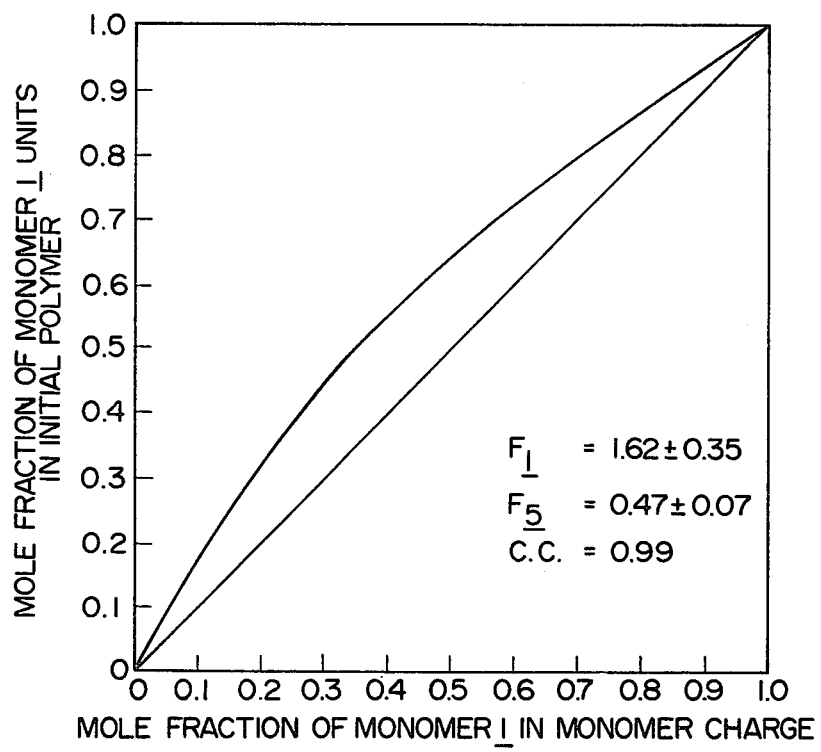

The measurement of reactivity ratios is mentioned in Example 1. FIGS. 1, 2 and 3 illutrate the employment of reactivity ratios in formulating copolymers in accordance with the invention. In each of these figures abscissae represent the mol fraction of the indicated monomer in the charge and ordinates represent the instantaneous mol fraction of such monomer in the resulting polymer. (The mol fraction of the other monomer is the difference between one and the mol fraction of the first monomer.) The reactivity ratios of the several monomers are given in the lower right quadrant of each figure. In each of the figures the 45° diagonal represents the ideal plot when the reactivity ratios of the two monomers are equal. The actual curves depart from this as shown. It will be seen that the actual curve in FIG. 2 for monomer 1/monomer 4 is very close to the ideal curve. The symbol "C.C." means correlation coefficient and indicates the closeness of fit of the actual curves with the experimental points.

The distribution of mer units derived from a Monomer I (e.g., monomer 1) and mer units derived from a Monomer II (e.g., THF) will depend upon the reactivity ratios of the monomers and upon the proportions in which they are mixed in the charge. For example, if a Monomer I is more reactive than a Monomer II and if I and II are charged in equimolar proportions, it can be expected that the head end of the copolymer will predominate in mer units from Monomer I, the tail end in units from Monomer II, and that the mid portion of the molecule will have a more nearly random distribution of mer units brought about by the fact that the predominance of molecules of Monomer II compensate for its lesser reactivity.

As shown in FIG. 2, monomers 1 and 4 have very nearly the same reactivity ratios and their curve lies very close to the ideal curve. A monomer 1/monomer 4 equimolar mixture, therefore, is more likely to result in a polymer having a random distribution of mer units throughout its length.

Such randomness is desirable, but not essential. It has been found, as is evident from the examples above, that a polymer having, in all probability, a certain degree of stereo regularity nevertheless has greatly improved formulating and fabricating properties.

As stated above copolymerization may be carried out in the conventional manner, e.g., as described in copending U.S. Pat. No. 3,436,359, but it is preferred to employ the method of my copending application Ser. No. 262,935. This method requires the formation of an adduct of a preinitiator precursor and a catalyst which, when mixed with a monomer forms an initiating species that undergoes chain extension. When, as is usually the case, the polymer is to be formulated by copolymerization and cross linking, e.g., with trimethylolethane and tolylene diisocyanate, it is necessary to form a polymer which is at least bifunctional, e.g., one which has terminal hydroxyl groups. This can be accomplished by using a bifunctional preinitiator precursor such as BDO which will provide an hydroxyl group at the head end of the polymer and by quenching the resulting living polymer with a similar diol or with water. If a bifunctional polymer is not required, e.g., if the polymer is to be used as such and is not to be copolymerized, such bifunctionality is not required; a bifunctional preinitiator precursor is not required; and quenching may be accomplished by a monofunctional entity such as a monohydric alcohol.

As stated above the energetic polymers (and the monomers from which they are derived) may have pendant energetic groups other than azido, e.g., nitro groups and nitrato groups. An example of a Monomer I having nitro groups is bis(nitromethyl) oxetane

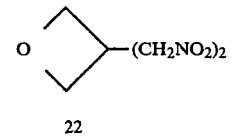

and an example of a Monomer I having a nitrato group is bis(nitratomethyl) oxetane

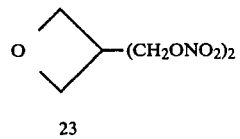

Each of the monomers may be copolymerized with a Monomer II, e.g., THF or oxetane or these two monomers may be copolymerized with one another. The syntheses of monomers 22 and 23 are described in the literature.

In carrying out copolymerization in accordance with my copending application Ser. No. 262,935 various preinitiator precursors, catalysts and solvents may be used such as the following:

PREINITIATOR PRECURSORS

Monohydric alcohols

Methyl, ethyl and normal and branched chain propyl, butyl, pentyl, hexyl and $C_7$ to $C_{20}$ alkanols; cycloaliphatic alcohols such as cyclohexanol and its ring substituted alkyl derivatives; aralkyl alcohols such as benzyl alcohol, phenyl ethyl alcohol, di- and tri-phenyl carbinols; furfuryl alcohol.

Polyhydric alcohols

Ethylene glycol, propylene glycol, 1,3-propanediol, glycerol, pentaerythritol, 1,4-butanediol; also the diols substituted by functional groups which may be energetic groups.

Ethers

Dimethyl, diethyl, di-n and isopropyl ethers; mixed ethers such as methyl ethyl ether; cyclic ethers where not used as monomers, e.g., difficultly polymerizable substituted tetrahydrofurans such as 2-methyl THF.

Carboxylic acids

Formic, acetic, propionic, butyric and other straight and branched chain acids of formula $C_nH_{2n+1}COOH$; aliphatic dicarboxylic acids such as succinic acid; aromatic carboxylic acids such as benzoic; o, n and p toluic acids; o, m and p chlorobenzoic acids, phthalic acid, salicylic acid, etc.

Sulfonic acids

Any of the above acids wherein $SO_3H$ replaces COOH.

Esters

Methyl, ethyl, straight and branched chain $C_3$ to $C_{20}$ alkyl esters of any of the carboxylic and sulfonic acids mentioned above; carbonic esters such as diethyl and dimethyl carbonates.

Ureas

Urea, methylol urea, dimethylol urea, other N-substituted ureas

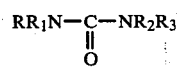

where R, $R_1$, $R_2$ and $R_3$ are selected from H, $C_1$ to $C_{12}$ alkyl, phenyl, benzyl, cyclohexyl, etc., at least one R being an essentially hydrocarbon group.

Amides

Amides of any of the carboxylic acids mentioned above including N-mono- and di-substituted amides

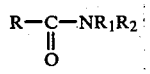

wherein R represents an organic group such as described above and in connection with carboxylic acids, $R_1$ and $R_2$ are selected from H, $C_1$ to $C_{20}$ alkyl, phenyl, benzyl, cyclohexyl, etc.; any of the amides listed in Morrison and Boyd, "Organic Chemicsty," 3d ed., page 660, published by Allyn and Bacon, Inc. of Boston.

Isocyanates

RNCO where R=$C_1$ to $C_{10}$ straight and branched chain alkyl, aryl such as phenyl and the tolyl isocyanates.

Amines $C_1$ to $C_{10}$ straight and branched chain alkylamines; aromatic amines, e.g., aniline; aliphatic cyclic amines, e.g., piperidine; and R-$NR_1R_2$ wherein R is an organic group and $R_1$ and $R_2$ are selected from H, straight and branched chain $C_1$ to $C_{10}$ alkyl, aryl (phenyl, o, m and p tolyl) and aralkyl, e.g., benzyl; cycloaliphatic amines, etc.; any of the amines listed in Morrison and Boyd, op. cit., page 729.

Acid anhydrides

Anhydrides of any of the carboxylic and sulfonic acids mentioned above; any of those listed in Morrison and Boyd, op. cit., page 660.

Ketones $RCOR_1$ where R and $R_1$ are $C_1$ to $C_{10}$ alkyl, phenyl, benzyl, cyclohexyl; any listed in Morrison and Boyd, op. cit., page 620.

Aldehydes

RCHO where R is as defined under "Ketones" above; also any listed in Morrison and Boyd, op. cit., page 620.

Analogues of the above

Sulfur, selenium and tellurium analogues of the above may be used, such as:

Thiols, e.g., $C_nH_{2n+1}SH$ where n=1 to 10

Thioethers, e.g., RS-$R_1$, R and $R_1$ defined as under the heading "Ketones".

Thioacids

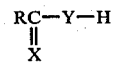

where one or both of X and Y are sulfur, the other, if not sulfur, being oxygen, R being an organic group as under the heading "Carboxylic Acids".

Thioureas: As under the heading "Ureas", doubly bonded O being substituted by S.

Thioamides: As under the heading "Amides", doubly bonded O being substuted by S.

Thioesters: As in "Thioacids" esterified as under "Esters."

Catalysts

Acids generally which are known to be effective for cationic polymerization of tetrahydrofuran and other cyclic ethers, e.g., strong acids and super acids such as $FSO_3H$ $ClSO_3H$ $HClO$ $HIO$ $CF_3SO_3H$.

Lewis acids such as $AlCl_3$ $BF_3$ $TiCl_4$ $ZnI_2$ $SiF_4$ $SbF_5$ $PF_5$

AsF$_5$

SbCl$_5$.

In general any substance known to catalyze cationic polymerization of monomers may be used. Many are described in scientific journals, in texts and patent literature, e.g., British Pat. No. 1,120,304 to Minnesota Mining and Manufacturing Company and literature referred to in such patent.

Solvents

Any solvent known to be compatible with cationic polymerization as to solubility of reactants, stability of the cation formed on initiation, etc., may be used. Usually it will be a polar aprotic solvent. In addition to solvents mentioned in the specific examples, suitable solvents include
Methylene chloride
Methyl chloride
Ethylene chloride, ClCH$_2$—CH$_2$Cl
Nitromethane
Chlorinated and fluorinated aromatic hydrocarbons such as chlorobenzene and fluorobenzene.

It will, therefore, be apparent that new and useful energetic copolymers and new and useful methods of preparing such copolymers have been provided.

What is claimed is:

1. A method of forming an energetic polymer having pendant energetic groups which comprises:
   (a) providing a Monomer I which is a cyclic oxide containing two to five carbon atoms in the oxide ring, said Monomer I, when homopolymerized, resulting in a polymer which is crystalline or viscous at temperatures normally used in formulations, said energeric group being one which decomposes without combustion at a temperature of about 180° C. to 250° C. to release a gas under pressure
   (b) providing also a Monomer II which is a cyclic oxide containing two to five carbon atoms in the oxide ring and which differs from Monomer I and is copolymerizable with Monomer I to produce a copolymer which is less crystalline or viscous than the homopolymer of Monomer I and
   (c) copolymerizing Monomers I and II in proportions such that the resulting copolymer has a substantially diminished crystallinity or viscosity compared to the homopolymer of Monomer I, said copolymerization being a cationic polymerization initiated by an adduct of a preinitiator precursor and a catalyst effective for cationic polymerization, and wherein such adduct and Monomers I and II are employed in proportions of one mol of adduct to n mols of I and II combined, n being a small number and the proportion of adduct greatly exceeding that required as a catalyst, the polymerization being allowed to go to completion.

2. The method of claim 1 wherein the preinitiator precursor is a polyol and the resulting living polymer is quenched with water or a polyol, resulting in a polymer having an hydroxyl group at each end.

3. The method of claim 2 wherein Monomer I is an azido substituted cyclic oxide and Monomer II is a nonenergetic cyclic oxide.

4. The method of claim 2 wherein both Monomers I and II are energetic.

5. The method of claim 4 wherein the energetic monomers have pendant azido groups.

6. The method of claim 4 wherein the energetic monomers have pendant nitro groups.

7. The method of claim 4 wherein the energetic monomers have pendant nitrato groups.

8. A copolymer comprising a chain of mer units resulting from the ring opening of a Monomer I which is a cyclic oxide containing two to five carbon atoms in the oxide ring and which contains also a pendant energetic group which decomposes without combustion at a temperature of about 180° C. to 230° C. and in so doing releases gas and (2) mer units resulting from the ring opening of a Monomer II which is a cyclic oxide containing two to five carbon atoms in the oxide ring, Monomer II differing from Monomer II; Monomer I, which homopolymerized, resulting in a polymer which is crystalline or viscous, the mer units derived from Monomer II being present in proportions sufficient that the copolymer has substantially diminished crystallinity or viscosity 9. The copolymer of claim 8 wherein the copolymer has terminal functional groups.

10. The copolymer of claim 9 wherein such terminal groups are hydroxyl.

* * * * *